(12) United States Patent
Britto (10) Patent No.: US 8,900,182 B2
(45) Date of Patent: Dec. 2, 2014

(54) BREAST PUMP AND METHOD OF USE

(71) Applicant: Tomy International, Inc., Dyersville, IA (US)

(72) Inventor: James J. Britto, Westport, MA (US)

(73) Assignee: Tomy International, Inc., Dyersville, IA (US)

( * ) Notice: Subject to any disclaimer, the term of this patent is extended or adjusted under 35 U.S.C. 154(b) by 104 days.

(21) Appl. No.: 13/707,878

(22) Filed: Dec. 7, 2012

(65) Prior Publication Data

US 2013/0102958 A1    Apr. 25, 2013

Related U.S. Application Data

(62) Division of application No. 13/144,873, filed as application No. PCT/US2010/021316 on Jan. 18, 2010, now Pat. No. 8,398,584.

(60) Provisional application No. 61/145,461, filed on Jan. 16, 2009.

(51) Int. Cl.
*A61M 1/06*    (2006.01)

(52) U.S. Cl.
CPC ........................................ *A61M 1/06* (2013.01)
USPC .......................................................... 604/74

(58) Field of Classification Search
CPC ........ A61M 1/06; A61M 1/064; A61M 1/066
USPC .................................................. 604/74, 75, 76
See application file for complete search history.

(56) References Cited

U.S. PATENT DOCUMENTS

| | | | |
|---|---|---|---|
| 316,584 A | 4/1885 | Turner |
| 532,236 A | 1/1895 | Hardesty |
| 684,078 A | 10/1901 | Martin |
| 823,316 A | 6/1906 | Andersen |
| 956,325 A | 4/1910 | Fey |
| 975,047 A | 11/1910 | Klein et al. |
| 1,113,942 A | 10/1914 | Anderson |
| 1,184,293 A | 5/1916 | Zeratsky |
| 1,184,631 A | 5/1916 | De Leon |
| 1,259,309 A | 3/1918 | Somers |
| 1,460,927 A | 7/1923 | Thompson et al. |

(Continued)

FOREIGN PATENT DOCUMENTS

| | | |
|---|---|---|
| CA | 2115824 | 8/1994 |
| CA | 2215368 | 2/1996 |

(Continued)

OTHER PUBLICATIONS

International Search Report and Written Opinion of the International Searching Authority, International Patent Application No. PCT/US2010/021316, mailed Aug. 23, 2010.

*Primary Examiner* — Aarti B Berdichevsky
(74) *Attorney, Agent, or Firm* — Michael Best & Friedrich LLP (57) ABSTRACT

A breast pump convertible between a single breast pump mode and a double breast pump mode. The breast pump includes a pump and a conduit assembly coupled to the pump and at least one breast shield. The breast pump is operable to convert between the single breast pump mode and the double breast pump mode while maintaining substantially the same vacuum level applied to one of the breasts.

17 Claims, 6 Drawing Sheets

(56) References Cited

U.S. PATENT DOCUMENTS

| | | |
|---|---|---|
| 1,596,520 A | 8/1926 | Eskholme et al. |
| 1,644,257 A | 10/1927 | Lasker |
| 1,670,610 A | 5/1928 | Colby |
| 2,060,063 A | 11/1936 | Frimand |
| 2,222,811 A | 11/1940 | Dinesen |
| 2,419,795 A | 4/1947 | Saunders |
| 2,522,108 A | 9/1950 | Flagg |
| 2,542,505 A | 2/1951 | Gascoigne |
| 2,545,857 A | 3/1951 | Perkins et al. |
| 3,233,607 A | 2/1966 | Bolie |
| 3,238,937 A | 3/1966 | Stein |
| 3,382,867 A | 5/1968 | Reaves |
| 3,587,567 A | 6/1971 | Schiff |
| 3,738,363 A | 6/1973 | Lunas et al. |
| 3,782,385 A | 1/1974 | Loyd |
| 3,797,734 A | 3/1974 | Fleury et al. |
| 3,822,703 A | 7/1974 | Davisson |
| 3,830,238 A | 8/1974 | Kurtz et al. |
| 3,911,920 A | 10/1975 | Susinn |
| 3,931,795 A | 1/1976 | Duncan |
| 3,977,405 A | 8/1976 | Yanase |
| 3,990,816 A | 11/1976 | Kohler et al. |
| 4,249,481 A | 2/1981 | Adams |
| 4,263,912 A | 4/1981 | Adams |
| 4,311,141 A | 1/1982 | Diamond |
| 4,323,067 A | 4/1982 | Adams |
| 4,486,157 A | 12/1984 | Hayashi |
| 4,501,585 A | 2/1985 | Friedman |
| 4,573,969 A | 3/1986 | Schlensog et al. |
| 4,583,970 A | 4/1986 | Kirchner |
| 4,607,596 A | 8/1986 | Whittlestone et al. |
| 4,634,430 A | 1/1987 | Polaschegg |
| 4,673,388 A | 6/1987 | Schlensog et al. |
| 4,680,028 A | 7/1987 | Stuart |
| 4,705,504 A | 11/1987 | Viers |
| 4,759,747 A | 7/1988 | Aida et al. |
| 4,772,262 A | 9/1988 | Grant et al. |
| 4,775,366 A | 10/1988 | Rosenblatt |
| 4,794,915 A | 1/1989 | Larsson |
| 4,799,922 A | 1/1989 | Beer et al. |
| 4,799,924 A | 1/1989 | Rosenblatt |
| 4,799,925 A | 1/1989 | Rosenblatt |
| 4,813,932 A | 3/1989 | Hobbs |
| 4,857,051 A | 8/1989 | Larsson |
| 4,883,464 A | 11/1989 | Morifuki |
| 4,898,578 A | 2/1990 | Rubalcaba, Jr. |
| 4,929,229 A | 5/1990 | Larsson |
| 4,941,433 A | 7/1990 | Hanauer |
| 4,950,236 A | 8/1990 | Wilson |
| 4,961,726 A | 10/1990 | Richter |
| 4,964,851 A | 10/1990 | Larsson |
| 5,007,899 A | 4/1991 | Larsson |
| 5,009,638 A | 4/1991 | Riedweg et al. |
| 5,049,126 A | 9/1991 | Larsson |
| 5,076,769 A | 12/1991 | Shao |
| 5,100,406 A | 3/1992 | Panchula |
| 5,104,374 A | 4/1992 | Bishko et al. |
| 5,178,095 A | 1/1993 | Mein |
| 5,218,924 A | 6/1993 | Thompson et al. |
| 5,295,957 A | 3/1994 | Aida et al. |
| 5,304,129 A | 4/1994 | Forgach |
| 5,356,398 A | 10/1994 | Willis |
| 5,358,476 A | 10/1994 | Wilson |
| 5,368,583 A | 11/1994 | Fleury |
| 5,514,166 A | 5/1996 | Silver et al. |
| 5,542,921 A | 8/1996 | Meyers et al. |
| 5,547,470 A | 8/1996 | Johnson et al. |
| 5,571,084 A | 11/1996 | Palmer |
| 5,586,518 A | 12/1996 | Carrano |
| 5,590,648 A | 1/1997 | Mitchell et al. |
| 5,601,531 A | 2/1997 | Silver |
| 5,616,125 A | 4/1997 | Jelks |
| 5,676,525 A | 10/1997 | Berner et al. |
| 5,691,932 A | 11/1997 | Reiner et al. |
| 5,720,722 A | 2/1998 | Lockridge |
| 5,749,850 A | 5/1998 | Williams et al. |
| 5,776,098 A | 7/1998 | Silver et al. |
| 5,810,772 A | 9/1998 | Niederberger |
| 5,843,029 A | 12/1998 | Bachman et al. |
| D406,348 S | 3/1999 | Koehnke |
| 5,885,246 A | 3/1999 | Ford |
| 5,902,267 A | 5/1999 | Medo |
| 5,941,847 A | 8/1999 | Huber et al. |
| 5,947,923 A | 9/1999 | Uehara et al. |
| 5,954,690 A | 9/1999 | Larsson |
| 6,045,529 A | 4/2000 | Nuesch |
| 6,050,432 A | 4/2000 | Koehnke |
| 6,090,065 A | 7/2000 | Giles |
| 6,110,140 A | 8/2000 | Silver |
| 6,116,780 A | 9/2000 | Young et al. |
| 6,139,521 A | 10/2000 | Larsson |
| 6,152,896 A | 11/2000 | Bachman et al. |
| 6,257,847 B1 | 7/2001 | Silver et al. |
| 6,270,474 B1 | 8/2001 | Nuesch |
| 6,290,671 B1 | 9/2001 | Niederberger |
| 6,299,594 B1 | 10/2001 | Silver |
| 6,314,315 B1 | 11/2001 | Hung et al. |
| 6,328,082 B1 | 12/2001 | Lafond |
| 6,328,709 B1 | 12/2001 | Hung et al. |
| 6,355,012 B1 | 3/2002 | Nuesch |
| 6,379,327 B2 | 4/2002 | Lundy |
| 6,383,163 B1 | 5/2002 | Kelly et al. |
| 6,387,072 B1 | 5/2002 | Larsson et al. |
| 6,423,030 B1 | 7/2002 | Silver |
| 6,427,475 B1 | 8/2002 | Defelice et al. |
| 6,440,100 B1 | 8/2002 | Prentiss |
| 6,461,324 B1 | 10/2002 | Schlensog |
| 6,481,986 B1 | 11/2002 | Silver et al. |
| 6,497,677 B2 | 12/2002 | Silver |
| 6,500,143 B2 | 12/2002 | Suh |
| 6,547,756 B1 | 4/2003 | Greter et al. |
| 6,575,202 B2 | 6/2003 | Lafond |
| 6,579,258 B1 | 6/2003 | Atkin et al. |
| 6,585,686 B2 | 7/2003 | Cloud |
| 6,610,024 B1 | 8/2003 | Benatti |
| 6,616,000 B1 | 9/2003 | Renz |
| 6,629,936 B2 | 10/2003 | Hung et al. |
| 6,638,727 B1 | 10/2003 | Hung et al. |
| 6,652,484 B1 | 11/2003 | Hunckler et al. |
| 6,663,587 B2 | 12/2003 | Silver et al. |
| D484,970 S | 1/2004 | Renz et al. |
| 6,673,036 B1 | 1/2004 | Britto |
| 6,673,037 B1 | 1/2004 | Silver |
| 6,676,610 B2 | 1/2004 | Morton et al. |
| 6,676,631 B1 | 1/2004 | Greter |
| D486,223 S | 2/2004 | Robson et al. |
| 6,689,073 B2 | 2/2004 | Quay |
| 6,699,213 B1 | 3/2004 | Annis et al. |
| 6,702,167 B2 | 3/2004 | Annis |
| 6,705,108 B2 | 3/2004 | Defelice et al. |
| 6,705,920 B1 | 3/2004 | Engel |
| 6,706,012 B2 | 3/2004 | McKendry et al. |
| 6,712,785 B2 | 3/2004 | Morton et al. |
| 6,723,066 B2 | 4/2004 | Larsson et al. |
| 6,732,773 B2 | 5/2004 | Renz |
| 6,740,075 B2 | 5/2004 | Lebel et al. |
| D491,363 S | 6/2004 | Renz et al. |
| 6,749,582 B2 | 6/2004 | Britto et al. |
| 6,750,037 B2 | 6/2004 | Adair et al. |
| 6,763,857 B2 | 7/2004 | Brown |
| 6,764,377 B2 | 7/2004 | Gillan |
| 6,779,638 B2 | 8/2004 | Renz et al. |
| 6,808,517 B2 | 10/2004 | Greter et al. |
| 6,840,918 B1 | 1/2005 | Britto et al. |
| 6,866,558 B2 | 3/2005 | Luciano et al. |
| 6,884,229 B2 | 4/2005 | Renz |
| 6,887,210 B2 | 5/2005 | Quay |
| 6,887,218 B2 | 5/2005 | Warburton |
| 6,910,594 B2 * | 6/2005 | Foley et al. .................. 215/11.1 |
| D507,111 S | 7/2005 | Renz et al. |
| 6,921,379 B2 | 7/2005 | Greter et al. |
| 6,932,780 B2 | 8/2005 | Kozersky |
| 6,932,790 B2 | 8/2005 | McKendry et al. |
| 6,964,651 B1 | 11/2005 | McKendry |

(56) References Cited

U.S. PATENT DOCUMENTS

| | | |
|---|---|---|
| 6,974,361 B2 | 12/2005 | Cravaack et al. |
| 6,974,439 B1 | 12/2005 | McKendry |
| 6,974,440 B2 | 12/2005 | Silver |
| 6,988,930 B2 | 1/2006 | Gillan |
| 6,997,897 B1 | 2/2006 | Silver et al. |
| 6,999,840 B2 | 2/2006 | Brezina et al. |
| 7,004,339 B2 | 2/2006 | Renz |
| 7,008,400 B2 | 3/2006 | Silver et al. |
| 7,029,454 B2 | 4/2006 | Watanabe |
| 7,029,456 B2 | 4/2006 | Ware et al. |
| 7,101,350 B2 | 9/2006 | Ytteborg |
| 7,150,346 B2 | 12/2006 | Renz et al. |
| 7,160,273 B2 | 1/2007 | Greter et al. |
| 7,166,087 B2 | 1/2007 | Silver et al. |
| 7,201,735 B2 | 4/2007 | Atkin et al. |
| 7,223,255 B2 | 5/2007 | Myers et al. |
| 7,255,681 B1 | 8/2007 | Silver et al. |
| 7,267,662 B1 | 9/2007 | Kirchner |
| 7,311,106 B1 | 12/2007 | Burton |
| 7,326,184 B2 | 2/2008 | Rollin |
| 7,354,418 B2 | 4/2008 | Lee et al. |
| 7,357,782 B2 | 4/2008 | Rollin et al. |
| 7,381,197 B2 | 6/2008 | Kelly et al. |
| 7,396,339 B2 | 7/2008 | Britto et al. |
| 7,396,340 B2 | 7/2008 | Onuki et al. |
| 7,413,557 B2 | 8/2008 | Samson et al. |
| 7,440,786 B2 | 10/2008 | Hockersmith et al. |
| 7,471,994 B2 | 12/2008 | Ford et al. |
| 7,472,797 B2 | 1/2009 | Ostrowski |
| 7,479,125 B2 | 1/2009 | Tashiro |
| 7,559,915 B2 | 7/2009 | Dao et al. |
| 7,569,031 B2 | 8/2009 | Britto |
| 7,575,557 B2 | 8/2009 | Morton et al. |
| 7,611,399 B2 | 11/2009 | Brigham |
| 7,641,629 B2 | 1/2010 | Yuen |
| 7,662,127 B2 | 2/2010 | Silver et al. |
| 7,666,162 B2 | 2/2010 | Renz et al. |
| 7,682,334 B2 | 3/2010 | Greter et al. |
| 7,713,230 B2 | 5/2010 | Kataoka et al. |
| 7,727,182 B2 | 6/2010 | Silver |
| 7,749,188 B2 | 7/2010 | Tashiro et al. |
| 7,758,540 B2 | 7/2010 | Yamashita et al. |
| 7,766,865 B2 | 8/2010 | Rollin |
| 7,776,008 B2 | 8/2010 | Renz et al. |
| 7,776,009 B2 | 8/2010 | Renz et al. |
| 7,780,201 B2 | 8/2010 | Luzbetak et al. |
| 7,785,305 B2 | 8/2010 | Myers et al. |
| 7,789,865 B2 | 9/2010 | Myers et al. |
| 7,789,965 B2 | 9/2010 | Matsushita et al. |
| 7,806,855 B2 | 10/2010 | Kliegman et al. |
| 7,811,248 B2 | 10/2010 | Bjorge |
| 7,819,839 B2 | 10/2010 | Gillan |
| 7,824,361 B2 | 11/2010 | Luzbetak et al. |
| 7,824,362 B2 | 11/2010 | Annis et al. |
| 7,824,363 B2 | 11/2010 | Myers |
| 7,833,190 B1 | 11/2010 | Hall |
| 7,835,230 B1 | 11/2010 | Chang |
| 7,875,000 B2 | 1/2011 | Krebs et al. |
| 7,887,507 B2 | 2/2011 | Shemesh et al. |
| 7,912,674 B2 | 3/2011 | Killoren Clark et al. |
| 7,945,452 B2 | 5/2011 | Fathallah et al. |
| 7,972,297 B2 | 7/2011 | Bryan et al. |
| 7,988,661 B2 | 8/2011 | Silver et al. |
| 8,052,634 B2 | 11/2011 | Thommen et al. |
| 8,052,635 B1 | 11/2011 | Kelly et al. |
| 8,057,425 B1 | 11/2011 | Myers et al. |
| 8,070,715 B2 | 12/2011 | Quackenbush et al. |
| 8,070,716 B2 | 12/2011 | Sutrina et al. |
| 8,070,724 B2 | 12/2011 | Attolini et al. |
| 8,075,516 B2 | 12/2011 | Pfenniger et al. |
| 8,079,975 B2 | 12/2011 | Britto et al. |
| 8,096,824 B2 | 1/2012 | Luzbetak et al. |
| 8,096,970 B2 | 1/2012 | Annis et al. |
| 8,100,854 B2 | 1/2012 | Vogelin et al. |
| 8,109,901 B2 | 2/2012 | Bryan et al. |
| 8,118,772 B2 | 2/2012 | Dao et al. |
| 8,137,305 B2 | 3/2012 | Kelly et al. |
| 8,142,393 B2 | 3/2012 | Myers |
| 8,152,754 B2 | 4/2012 | Silver |
| 8,167,833 B2 | 5/2012 | Tashiro |
| 8,187,219 B1 | 5/2012 | Chiang |
| 8,187,227 B2 | 5/2012 | Luzbetak et al. |
| 8,192,396 B2 | 6/2012 | Annis et al. |
| 8,216,178 B2 | 7/2012 | Thommen |
| 8,216,179 B2 | 7/2012 | Bosshard et al. |
| 8,262,606 B2 | 9/2012 | Greter et al. |
| 8,398,584 B2 * | 3/2013 | Britto ............... 604/74 |
| 2002/0072701 A1 | 6/2002 | Nuesch |
| 2003/0069536 A1 | 4/2003 | Greter et al. |
| 2003/0139702 A1 | 7/2003 | Renz et al. |
| 2003/0204164 A1 * | 10/2003 | Britto et al. ............ 604/74 |
| 2004/0024352 A1 | 2/2004 | Renz et al. |
| 2004/0094498 A1 * | 5/2004 | Foley et al. ............ 215/11.3 |
| 2004/0127845 A1 | 7/2004 | Renz et al. |
| 2004/0249340 A1 | 12/2004 | Britto et al. |
| 2005/0159656 A1 | 7/2005 | Hockersmith et al. |
| 2005/0159701 A1 | 7/2005 | Conaway |
| 2005/0245860 A1 * | 11/2005 | Britto et al. ............ 604/74 |
| 2006/0195064 A1 | 8/2006 | Plahey et al. |
| 2007/0135761 A1 | 6/2007 | Cheng et al. |
| 2008/0009815 A1 | 1/2008 | Grabenkort et al. |
| 2008/0221495 A1 | 9/2008 | Steffens et al. |
| 2008/0255503 A1 * | 10/2008 | Quackenbush et al. ......... 604/74 |
| 2009/0099511 A1 * | 4/2009 | Sutrina et al. ............ 604/74 |
| 2009/0227855 A1 | 9/2009 | Hill et al. |
| 2009/0254029 A1 | 10/2009 | Tashiro et al. |
| 2009/0270810 A1 | 10/2009 | Debelser et al. |
| 2010/0016789 A1 | 1/2010 | Bosshard et al. |
| 2010/0049119 A1 | 2/2010 | Norman et al. |
| 2010/0094078 A1 | 4/2010 | Weston |
| 2010/0100037 A1 | 4/2010 | Cozmi et al. |
| 2010/0228222 A1 | 9/2010 | Williams et al. |
| 2011/0060328 A1 | 3/2011 | Skwarek et al. |
| 2011/0087162 A1 * | 4/2011 | Luzbetak et al. ............ 604/74 |
| 2011/0144569 A1 | 6/2011 | Britton et al. |
| 2011/0172524 A1 | 7/2011 | Hidem et al. |
| 2011/0270163 A1 | 11/2011 | Britto |
| 2011/0275984 A1 | 11/2011 | Biewer et al. |
| 2012/0004603 A1 | 1/2012 | Harari et al. |
| 2012/0029424 A1 | 2/2012 | Greter et al. |

FOREIGN PATENT DOCUMENTS

| | | |
|---|---|---|
| CA | 2487980 | 12/2003 |
| DE | 540934 | 12/1931 |
| DE | 2451953 | 5/1976 |
| DE | 2807646 | 8/1978 |
| DE | 3228725 | 2/1984 |
| EP | 0123269 | 10/1984 |
| EP | 0604070 | 6/1994 |
| EP | 0611578 | 8/1994 |
| EP | 0733376 | 9/1996 |
| FR | 599054 | 1/1926 |
| GB | 271857 | 10/1927 |
| GB | 660283 | 11/1951 |
| GB | 762701 | 12/1956 |
| GB | 2082920 | 3/1982 |
| GB | 2127293 | 4/1984 |
| JP | 8198279 | 8/1996 |
| JP | 2001259023 | 9/2001 |
| KR | 10-1099799 | 12/2011 |
| NZ | 168234 | 9/1921 |
| SE | 158976 | 5/1957 |
| WO | 9011097 | 10/1990 |
| WO | 9634638 | 11/1996 |
| WO | 9705913 | 2/1997 |
| WO | 9944650 | 9/1999 |
| WO | 9951882 | 10/1999 |
| WO | 0010625 | 3/2000 |
| WO | 0041744 | 7/2000 |
| WO | 0041745 | 7/2000 |
| WO | 0057934 | 10/2000 |

* cited by examiner

BREAST PUMP AND METHOD OF USE

RELATED APPLICATIONS

This application is a divisional of U.S. patent application Ser. No. 13/144,873 filed on Jul. 15, 2011, which is a 35 U.S.C. §371 application of PCT Application No. PCT/US2010/021316 filed on Jan. 18, 2010, which claims priority to U.S. Provisional patent application Ser. No. 61/145,461 filed on Jan. 16, 2009, the entire contents of which are incorporated herein by reference.

BACKGROUND OF THE INVENTION

Nursing mothers frequently use mechanized pumps to express milk from their breasts for bottle-feeding their infant children. Nursing mothers want a mechanized pump that provides comfort, efficiency, ease of use (including portability) and discretion. Some such pumps are manually operated, in that the pumping action is motivated by reciprocating a piston or lever by hand, or compressing a flexible bulb. Often the pump lever is located directly on a structure that must be held against the breast while the lever is reciprocated. Other such pumps are electrically operated, and are generally considered less fatiguing than manual pumps. Between uses, careful cleaning is required to keep the pump components that come in contact with breast milk sanitary.

Pumped milk must typically be refrigerated if it will not be immediately consumed. It is common to store such milk in sanitized bottles or bags. Improvements to pump constructions and pumping methods are desired, for comfortable and sanitary use

SUMMARY OF THE INVENTION

In one embodiment, the invention provides a double breast pump operable to convert to a single breast pump with the application of vacuum on the breast in the single mode being substantially the same as the application of vacuum on one of the breasts in the double mode.

In one embodiment, the present invention provides a breast pump comprising a pump, and a conduit assembly in fluid communication with the pump and a breast shield. The conduit assembly includes a first connector having a first port, a second port, and a third port, the first port in fluid communication with the pump and the second port; a second connector having a fourth port, a fifth port, a sixth port, a seventh port, and an eighth port; the fifth port in fluid communication with the second port, the sixth port, and the seventh port; the fourth port in fluid communication with the third port and the eighth port; and the sixth port in fluid communication with the seventh port and the breast shield.

In another embodiment, the present invention provides a method of converting between a single breast pump and a double breast pump. The method comprises connecting a conduit assembly to a pump, where the conduit assembly includes a first connector having a first port, a second port, and a third port, the first port in fluid communication with the pump and the second port; a second connector having a fourth port, a fifth port, a sixth port, a seventh port, and an eighth port; the fifth port in fluid communication with the second port, the sixth port, and the seventh port; a first conduit in fluid communication with the sixth port and a first breast shield; and a second conduit having a first end in fluid communication with the seventh port and a second end. The method further includes selecting one of a double breast pump mode by connecting the second end of the second conduit to a second breast shield and blocking the eighth port and a single breast pump mode by connecting the second end of the second conduit to the eighth port, and activating the pump to alternate between a first cycle and a second cycle to express fluid from at least one breast.

In yet another embodiment, the present invention provides a method of operating a breast pump. The method comprises activating a motor in communication with a pump, initiating a first cycle of the pump to apply a vacuum to a breast, activating a solenoid valve to initiate a second cycle of the pump to release the vacuum applied to the breast, stopping the motor just prior to activating the solenoid valve to allow the vacuum to stop increasing, and transmitting air to the breast after the solenoid valve is activated to at least partially release the vacuum applied to the breast.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

Figure 1:
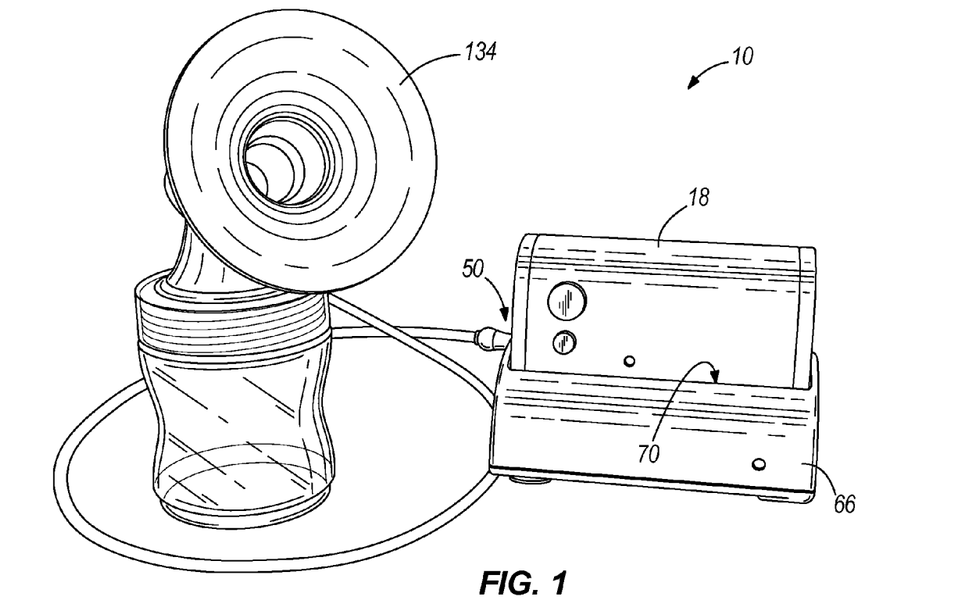
FIG. 1 is a perspective view of a single breast pump according to an embodiment of the present invention.
Figure 2:
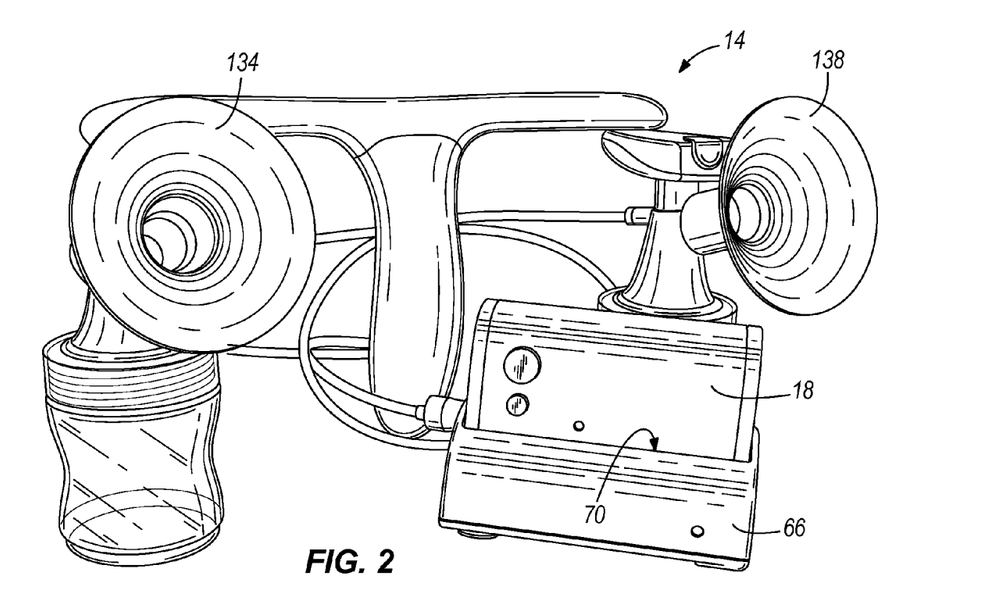
FIG. 2 is a perspective view of a double breast pump according to an embodiment of the present invention.

FIG. 1 illustrates a single breast pump 10 according to an embodiment of the present invention, and FIG. 2 illustrates a double breast pump 14 according to an embodiment of the present invention. The breast pumps 10, 14 include a housing 18 for supporting various components configured to operate the breast pumps 10, 14. The housing 18, further illustrated in FIGS. 3-4, supports a plurality of pumps 22 and a motor 26 connected to each of the pumps 22 and operable to control activation of the pumps 22. The housing 18 also supports a plurality of conduits 30 connected to an output port 34 of each of the pumps 22 and a 3-way conduit connector 38 joining the conduits 30 to a single conduit 42. The housing 18 also supports a solenoid valve 46 connected to the conduit 42 and is operable to control the fluid flow in the conduits 30, 42. The housing 18 also can include one or more batteries operable to provide power to the motor 26.

Figure 3:
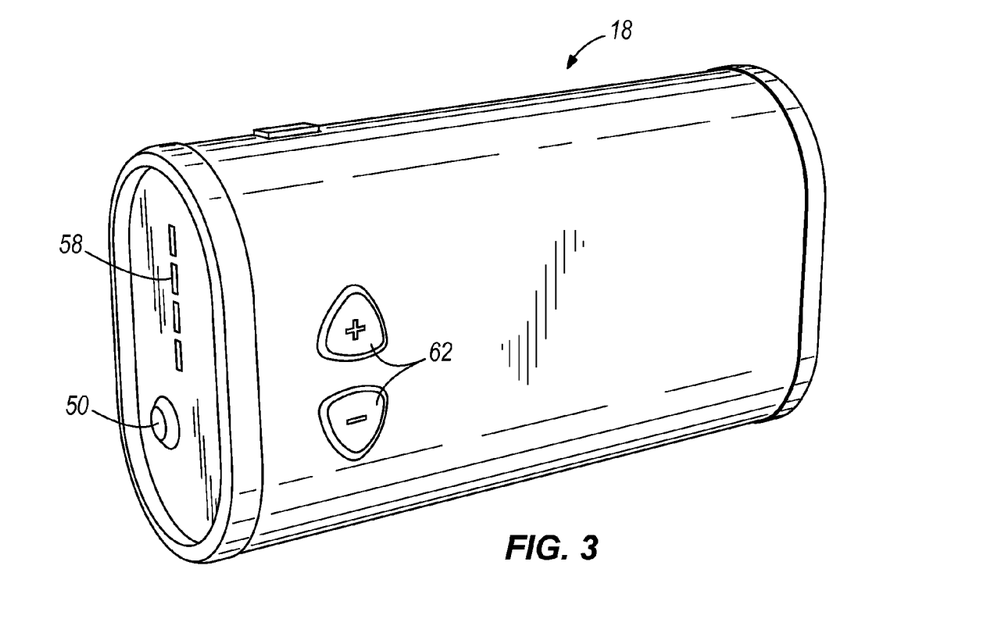
FIG. 3 is a perspective view of a housing of the breast pumps illustrated in FIGS. 1-2.
Figure 4:
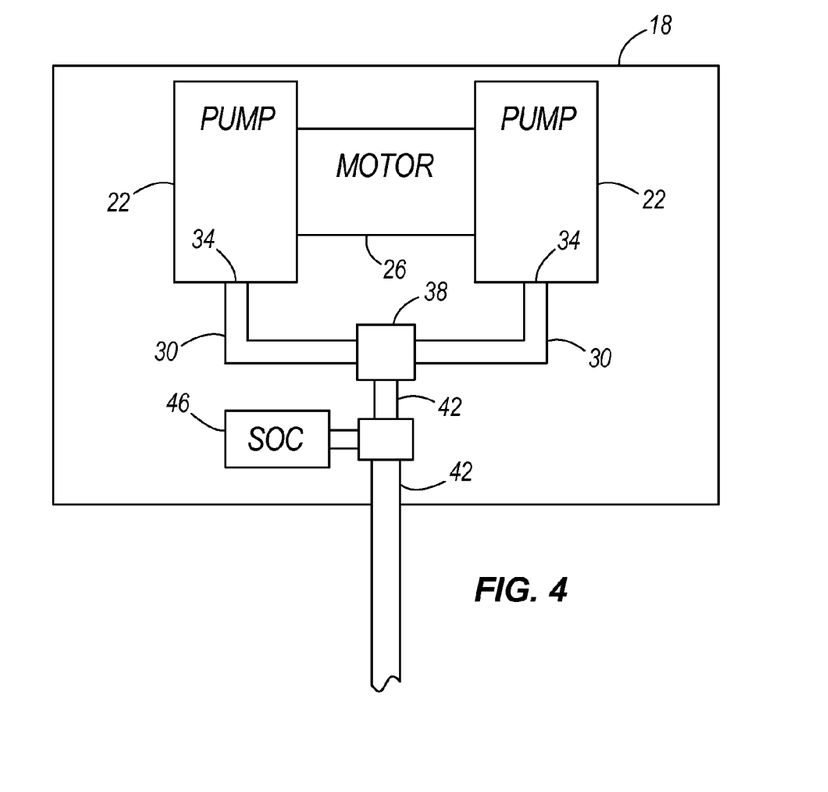
FIG. 4 is a block diagram of components supported by the housing illustrated in FIG. 3.

The housing 18 also includes an input port 50 configured to receive a conduit assembly 54 (discussed further below) and a display 58 operable to indicate whether the breast pump 10, 14 is powered and the pumping mode of the breast pump 10, 14. The housing 18 also includes a plurality of actuators 62 operable to control an amount of vacuum generated by one or more of the pumps 22 and applied to the breast.

The breast pumps 10, 14 include a cradle 66 having a recess 70 configured to receive and support the housing 18. The cradle 66 can include one or more batteries with suitable circuitry operable to provide power to the motor 26. In other constructions, the cradle 66 can include circuitry operable to transfer power from a standard outlet to the motor 26. In other constructions, the cradle 66 can include both the circuitry and the one or more batteries in order to power the motor 26. The cradle 66 can include a connector positioned within the recess 70 and configured to mate with a corresponding connector on the housing 18 where power is transferred from the cradle 66 to the housing 18.

Figure 5:
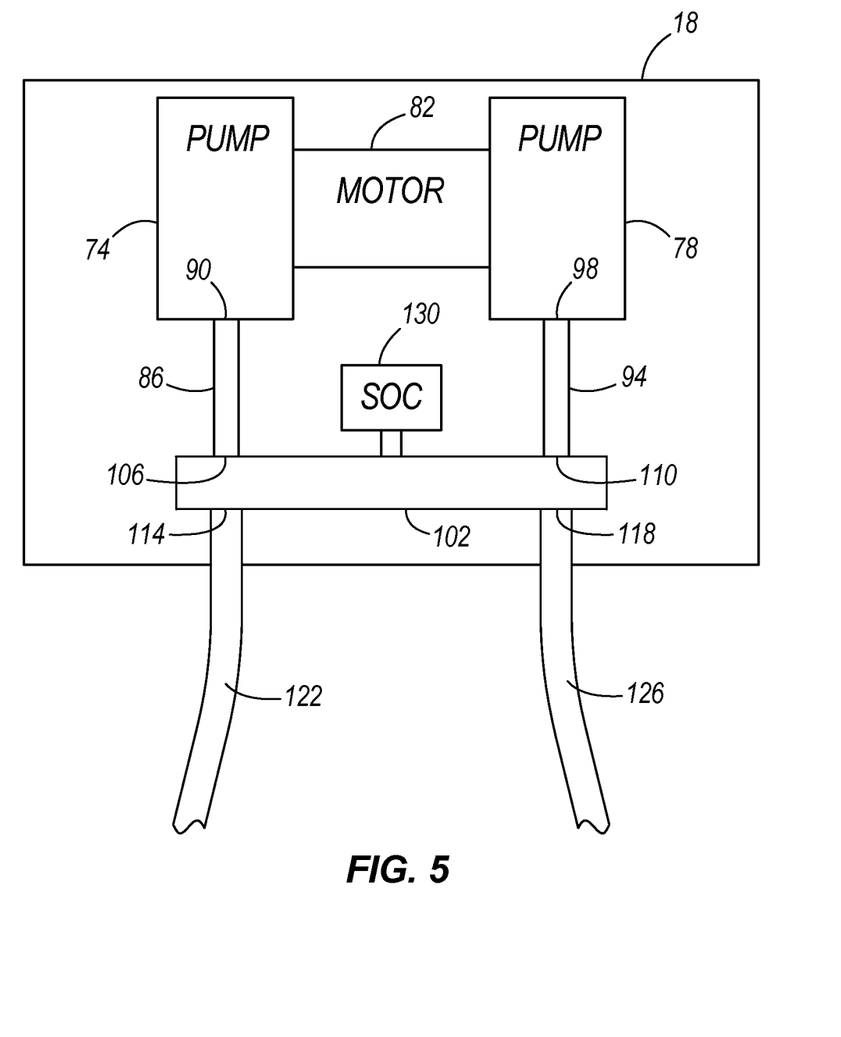
FIG. 5 is a block diagram of components supported by the housing illustrated in FIG. 3 according to another construction of the invention.

In an alternative construction illustrated in FIG. 5, the housing 18 can support the components described above in an alternative arrangement. As illustrated, the housing 18 can support a first pump 74, a second pump 78, and a motor 82 connected to each of the pumps 74, 78 and is operable to control activation of the pumps 74, 78. The housing 18 also can support a first conduit 86 connected to an output port 90 of the first pump 74 and a second conduit 94 connected to an output port 98 of the second pump 78. A distal end of the first conduit 86 and a distal end of the second conduit 94 are connected to and in fluid communication with a connector 102 at a first input 106 and a second input 110, respectively. The connector 102 includes a first output 114 and a second output 118 in fluid communication with a conduit 122 and a conduit 126, respectively. The housing 18 can further support a solenoid valve 130 connected to the connector 102 and operable to independently control the fluid flow between the first pump 74 and the conduit 122 and between the second pump 78 and the conduit 126. In this construction, the housing 18 can include two input ports 50.

The breast pump 10 includes a breast shield 134 in communication with the input port 50 on the housing 18 through the conduit assembly 54. Similarly, the breast pump 14 includes a first breast shield 134 and a second breast shield 138 in communication with the input port 50 on the housing 18 through the conduit assembly 54 to allow the user to double pump. The vacuum developed by one or both of the pumps 22 is applied to a human breast supported in the breast shield 134 and/or the breast shield 138 to expel breast milk from the breast to a container supported by the breast shield 134, 138.

The conduit assembly 54, illustrated in FIGS. 6A-B and 7A-B, includes a first connector or adapter 142 connected to the input port 50 on the housing 18. The first connector 142 includes a first port 146, a second port 150, and a third port 154. The first port 146 is in fluid communication with the input port 50 and the second port 150. The conduit assembly 54 also includes a second connector 158 having a first port 162 (i.e., a fourth port of the conduit assembly 54), a second port 166 (i.e., a fifth port of the conduit assembly 54), a third port 170 (i.e., a sixth port of the conduit assembly 54), a fourth port 174 (i.e., a seventh port of the conduit assembly 54), and a fifth port 178 (i.e., an eighth port of the conduit assembly 54). The second port 166 of the second connector 158 is in fluid communication with the second port 150 of the first connector 142 via a conduit 182. The first port 162 of the second connector 158 is in fluid communication with the third port 154 of the first connector 142 via a conduit 186 and the fifth port 178 of the second connector 158. The fifth port 178 is closed with a plug.

The second port 166 of the second connector 158 also is in fluid communication with the third port 170 and the fourth port 174 of the second connector 158. The third port 170 and the fourth port 174 are also in fluid communication. The third port 170 is in fluid communication with one of the first breast shield 134 and the second breast shield 138. The fourth port 174 is in fluid communication with the other of the first breast shield 134 and the second breast shield 138.

Figure 6A:
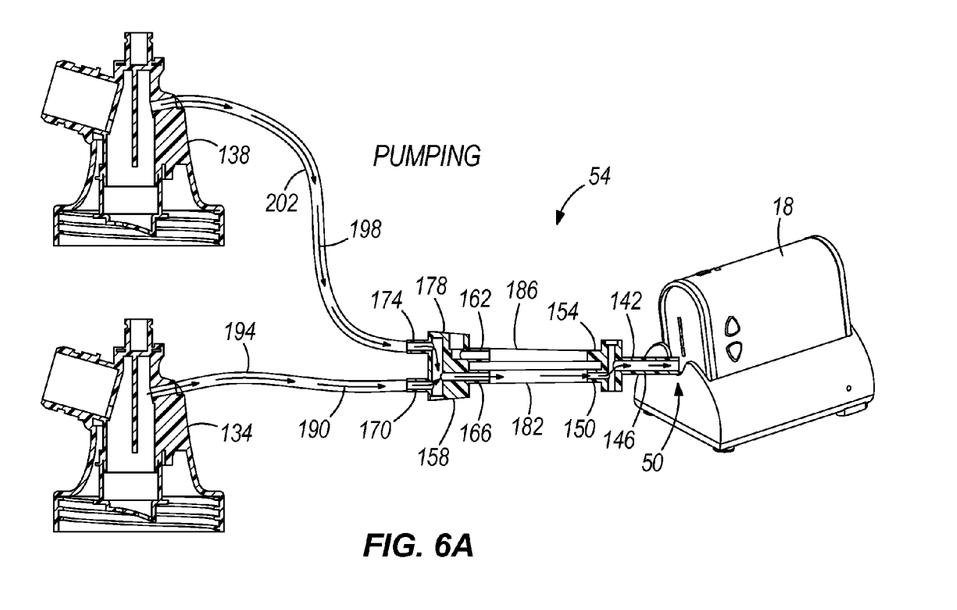
FIG. 6A is a schematic view of fluid flow during a vacuum cycle of the double breast pump illustrated in FIG. 2.
Figure 6B:
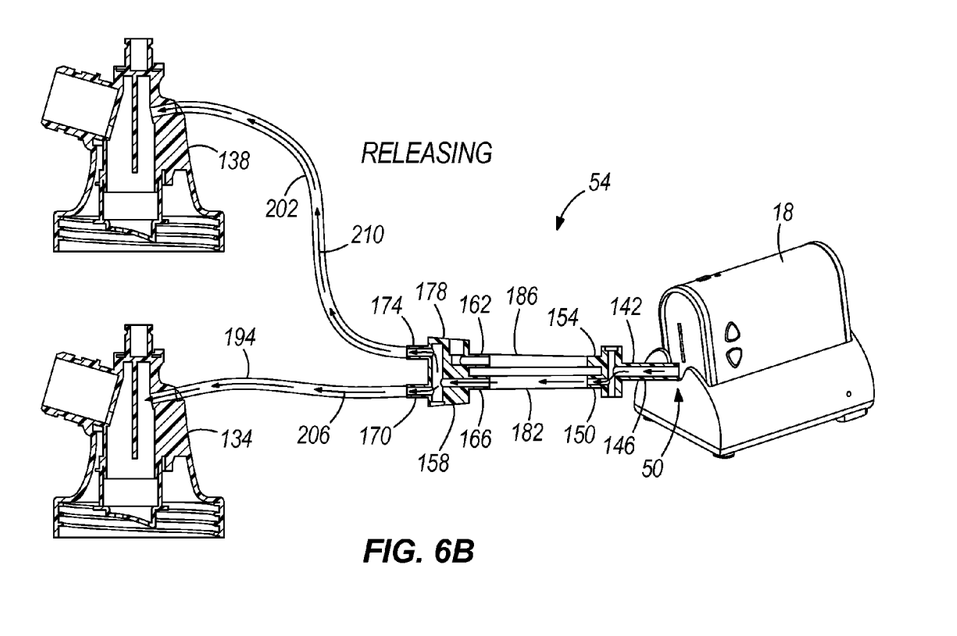
FIG. 6B is a schematic view of fluid flow during a release cycle of the double breast pump illustrated in FIG. 2.

In the breast pump configuration utilizing the double breast pump 14, the fluid flow during operation of the breast pump 14 is illustrated in FIGS. 6A-B. FIG. 6A illustrates a pumping or suction cycle of the breast pump 14. During operation of the pumping cycle, the pump 22 applies a vacuum to the input port 50, which is then applied to the human breasts supported by the first breast shield 134 and the second breast shield 138 as illustrated in FIG. 6A. The vacuum is applied to the human breast in the first breast shield 134 via a pathway 190 indicated by the arrows. The pathway 190 is generally defined by the input port 50 on the housing 18, the first port 146 on the first connector 142, the second port 150 on the first connector 142, the conduit 182, the second port 166 on the second connector 158, the third port 170 on the second connector 158, and a conduit 194.

The vacuum also is applied to the human breast in the second breast shield 138 via a pathway 198 indicated by the arrows. The pathway 198 is generally defined by the input port 50 on the housing 18, the first port 146 on the first connector 142, the second port 150 on the first connector 142, the conduit 182, the second port 166 on the second connector 158, the fourth port 174 on the second connector 158, and a conduit 202.

FIG. 6B illustrates a release cycle of the breast pump 14. During the release cycle, the solenoid valve 46 opens to release the vacuum. When the solenoid valve 46 opens to release the pressure, the motor 26 stops to allow the pressure to stop increasing. Alternatively, when the solenoid valve 46 opens, the motor 26 stops to conserve electrical power and to provide a smoother pressure curve. When the solenoid valve 46 opens, air travels through the conduit assembly 54 that at least partially releases the vacuum applied to the breasts supported by the first breast shield 134 and the second breast shield 138. The air travels to the first breast shield 134 via a pathway 206 generally defined by the input port 50 on the housing 18, the first port 146 on the first connector 142, the second port 150 on the first connector 142, the conduit 182, the second port 166 on the second connector 158, the third port 170 on the second connector 158, and the conduit 194. The air travels to the second breast shield 138 via a pathway 210 generally defined by the input port 50 on the housing 18, the first port 146 on the first connector 142, the second port 150 on the first connector 142, the conduit 182, the second port 166 on the second connector 158, the fourth port 174 on the second connector 158, and the conduit 202.

Figure 7A:
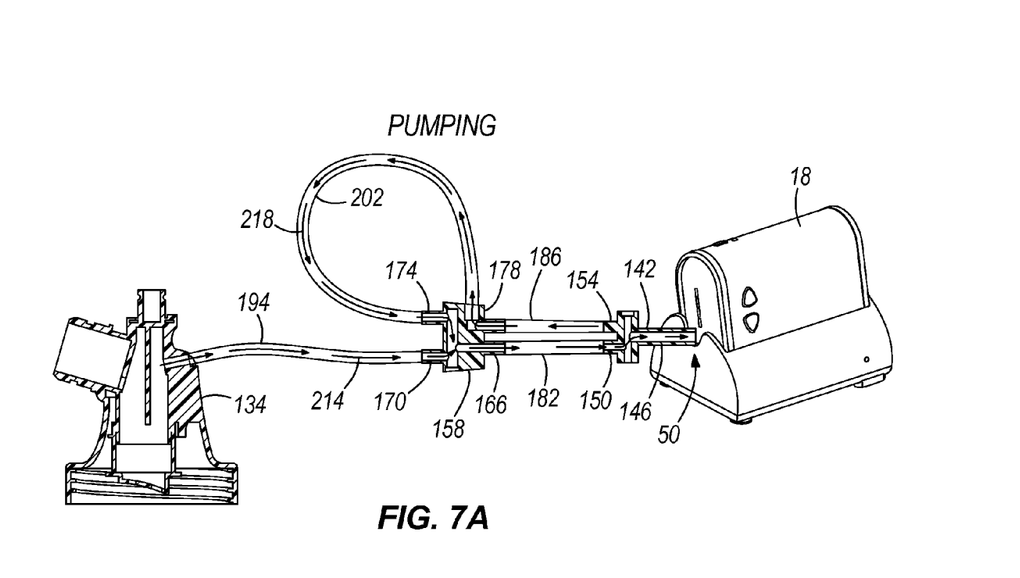
FIG. 7A is a schematic view of fluid flow during a vacuum cycle of the single breast pump illustrated in FIG. 1.
Figure 7B:
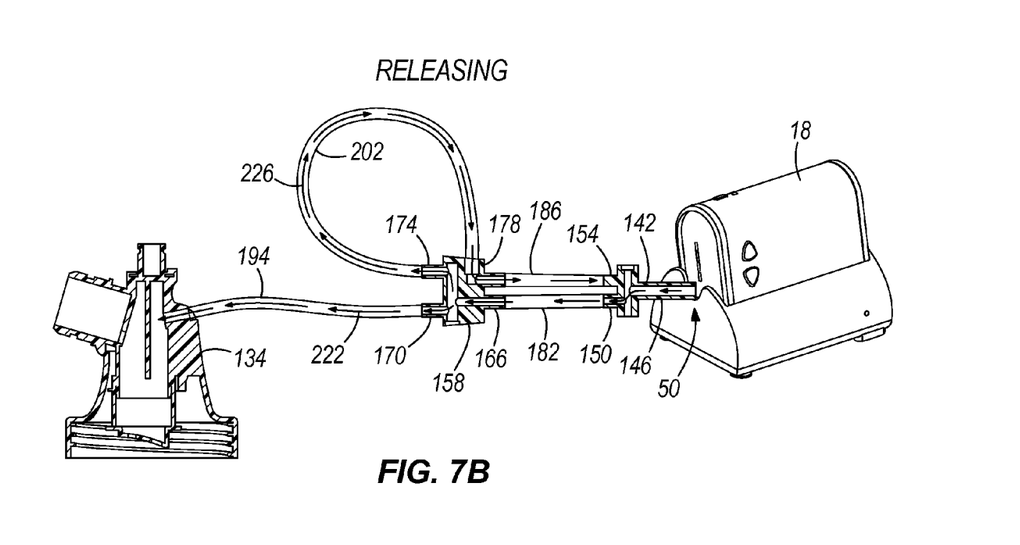
FIG. 7B is a schematic view of fluid flow during a release cycle of the single breast pump illustrated in FIG. 1.

A user of the double breast pump 14 can convert to the single pump 10 configuration by disconnecting one of the breast shields 134, 138. As illustrated in FIGS. 7A-B, the second breast shield 138 has been disconnected, but the first breast shield 134 could also be disconnected in lieu of the second breast shield 138. To convert to the single pump configuration, the conduit 202 is disconnected from the second breast shield 138 and is positioned within the fifth port 178 (after removing the plug in the fifth port 178) of the second connector 158. This conversion adds conduit length to the volume of fluid being evacuated from the first breast shield 134 during a vacuum cycle such that the vacuum applied to the breast supported by the first breast shield 134 is reduced or comparable to what the user feels at the same breast in the double pump configuration.

In the breast pump configuration utilizing the single breast pump 10, the fluid flow during operation of the breast pump 10 is illustrated in FIG. 7A-B. FIG. 7A illustrates a pumping or suction cycle of the breast pump 10. During operation of the pumping cycle, the pump 22 applies a vacuum to the input port 50, which is then applied to the human breast supported by the first breast shield 134 as illustrated in FIG. 7A. The vacuum is applied to the human breast in the first breast shield 134 via a pathway 214 indicated by the arrows. The pathway 214 is generally defined by the input port 50 on the housing 18, the first port 146 on the first connector 142, the second port 150 on the first connector 142, the conduit 182, the second port 166 on the second connector 158, the third port 170 on the second connector 158, and the conduit 194. The pathway 214 also includes a pathway 218 defined by third port 154 of the first connector 142, the conduit 186, the first port 162 on the second connector 158, the fifth port 178 on the second connector 158, the conduit 202, and the fourth port 174 on the second connector. The pathway 218 merges with the pathway 214 between the third port 170 and the fourth port 174 on the second connector 158.

FIG. 7B illustrates a release cycle of the breast pump 10. During the release cycle, the solenoid valve 46 opens to release the vacuum. When the solenoid valve 46 opens to release the pressure, the motor 26 stops to allow the pressure to stop increasing. Alternatively, when the solenoid valve 46 opens, the motor 26 stops to conserve electrical power and to provide a smoother pressure curve. When the solenoid valve 46 opens, air travels through the conduit assembly 54 to the first breast shield 134 via a pathway 222 generally defined by the input port 50 on the housing 18, the first port 146 on the first connector 142, the second port 150 on the first connector 142, the conduit 182, the second port 166 on the second connector 158, the third port 170 on the second connector 158, and the conduit 194. The pathway 222 also includes a pathway 226 defined by third port 154 of the first connector 142, the conduit 186, the first port 162 on the second connector 158, the fifth port 178 on the second connector 158, the conduit 202, and the fourth port 174 on the second connector. The pathway 226 merges with the pathway 222 between the third port 170 and the fourth port 174 on the second connector 158.

Figure 8:
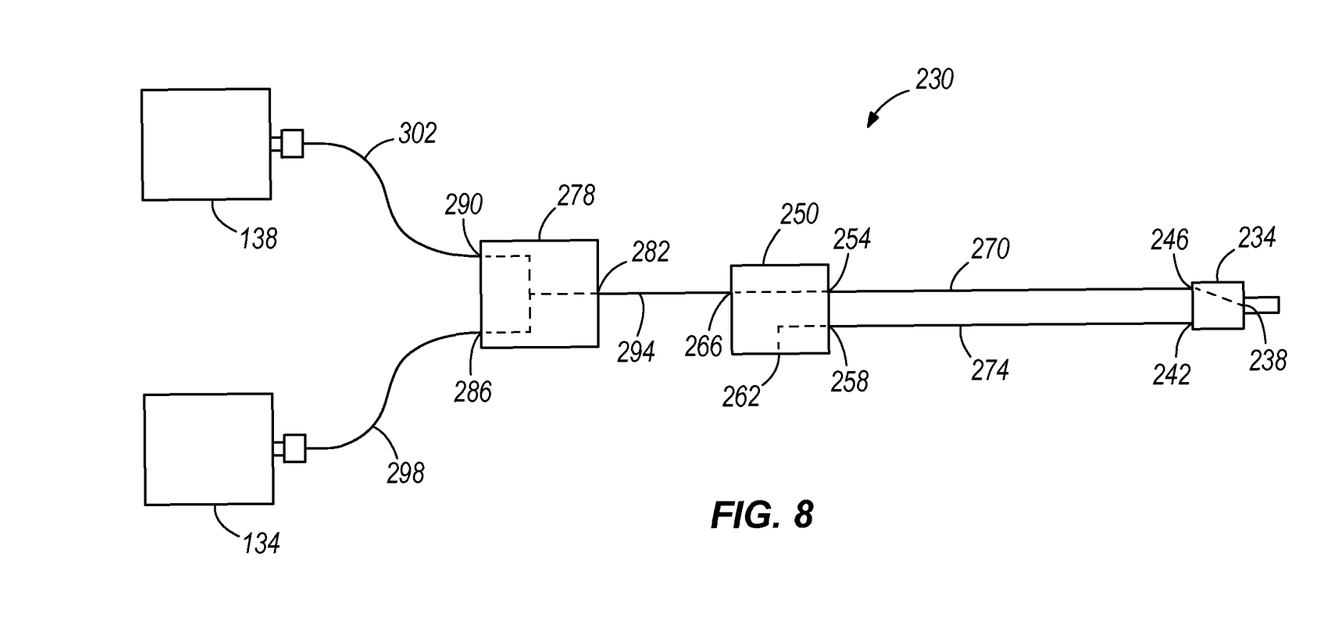
FIG. 8 is a block diagram of a conduit assembly according to another construction of the invention.

FIG. 8 illustrates a conduit assembly 230 according to an alternative construction. The conduit assembly 230 includes a first connector 234 in fluid communication with the input port 50 on the housing 18. The first connector 234 includes a first port 238, a second port 242, and a third port 246. The first port 238 is in fluid communication with the third port 246 and the input port 50. The conduit assembly 230 also includes a second connector 250 having a first port 254, a second port 258, a third port 262, and a fourth port 266. The first port 254 of the second connector 250 is in fluid communication with the third port 246 of the first connector 234 via a conduit 270. The second port 258 of the second connector 250 is in fluid communication with the second port 242 of the first connector 234 via a conduit 274 and the third port 262 of the second connector 250. The third port 262 is closed with a plug.

The conduit assembly 230 also includes a third connector 278 having a first port 282, a second port 286, and a third port 290. The first port 282 of the third connector 278 is in fluid communication with the fourth port 266 of the second connector 250 via a conduit 294, the second port 286, and the third port 290. The second port 286 of the third connector is in fluid communication with the first breast shield 134 via a conduit 298, and the third port 290 of the third connector 278 is in fluid communication with the second breast shield 138 via a conduit 302.

When converting from a double pump configuration to a single pump configuration, the user removes the plug in the third port 262 of the second connector 250, removes one of the conduits 298, 302, and positions the removed conduit 298, 302 into the third port 262 of the second connector 250.

Other suitable configurations of the conduit assembly 54 are also contemplated by the present invention. The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention.

Various features and advantages of the invention are set forth in the following claims.

What is claimed is:

1. A breast pump comprising:
   a pump; and
   a conduit assembly in fluid communication with the pump and a breast shield, the conduit assembly including
      a first connector having a first port, a second port, and a third port, the first port in fluid communication with the pump and the second port,
      a second connector having a fourth port, a fifth port, a sixth port, a seventh port, and an eighth port,
      the fifth port in fluid communication with the second port, the sixth port, and the seventh port,
      the fourth port in fluid communication with the third port and the eighth port, and
      the sixth port in fluid communication with the seventh port and the breast shield.

2. The breast pump of claim 1 further comprising a second pump in fluid communication with the conduit assembly.

3. The breast pump of claim 2 further comprising a motor coupled to the first pump and the second pump and configured to control activation of the first pump and the second pump.

4. The breast pump of claim 2 further comprising a third connector having a first port in communication with the first pump, a second port in communication with the second pump, and a third port in communication with the conduit assembly.

5. The breast pump of claim 1 further comprising a solenoid valve in fluid communication with the pump and the conduit assembly, the solenoid valve configured to control the fluid flow between the pump and the conduit assembly.

6. The breast pump of claim 1 further comprising a user interface configured to control an amount of vacuum generated by the pump.

7. The breast pump of claim 1 wherein the conduit assembly further includes the seventh port in fluid communication with one of a second breast shield and the eighth port.

8. The breast pump of claim 7 wherein the eighth port is blocked from fluid communication with the environment when the seventh port is in fluid communication with the second breast shield.

9. The breast pump of claim 1 wherein the conduit assembly further includes a conduit in fluid communication with the third port and the eighth port.

10. The breast pump of claim 1 wherein the seventh port is in fluid communication with the third port when the seventh port is in fluid communication with the eighth port.

11. A method of converting between a single breast pump and a double breast pump, the method comprising:
    connecting a conduit assembly to a pump, the conduit assembly including
        a first connector having a first port, a second port, and a third port, the first port in fluid communication with the pump and the second port,
        a second connector having a fourth port, a fifth port, a sixth port, a seventh port, and an eighth port,
        the fifth port in fluid communication with the second port, the sixth port, and the seventh port,
        a first conduit in fluid communication with the sixth port and a first breast shield, and
        a second conduit having a first end in fluid communication with the seventh port and a second end;
    selecting one of a double breast pump mode by connecting the second end of the second conduit to a second breast shield and blocking the eighth port and a single breast pump mode by connecting the second end of the second conduit to the eighth port; and
    activating the pump to alternate between a first cycle and a second cycle to express fluid from at least one breast.

12. The method of claim 11 wherein the first cycle applies a vacuum to at least one breast.

13. The method of claim 12 wherein in the single breast pump mode air is removed from a first pathway defined by the first breast shield, the first conduit, the sixth port, the fifth port, a third conduit, the second port, the first port, and a fourth conduit between the first port and the pump and a second pathway defined by the third port, a fifth conduit, the fourth port, the eighth port, the second conduit, the seventh port, the fifth port, the third conduit, the second port, the first port, and the fourth conduit.

14. The method of claim 12 wherein in the double breast pump mode air is removed from a first pathway defined by the first breast shield, the first conduit, the sixth port, the fifth port, a third conduit, the second port, the first port, and a fourth conduit between the first port and the pump and a second pathway defined by the second breast shield, the second conduit, the seventh port, the fifth port, the third conduit, the second port, the first port, and the fourth conduit.

15. The method of claim 11 wherein the second cycle releases a vacuum from at least one breast.

16. The method of claim 15 wherein in the single breast pump mode air is transmitted to the breast via a pathway defined by the first breast shield, the first conduit, the sixth port, the fifth port, a third conduit, the second port, the first port, and a fourth conduit between the first port and the pump.

17. The method of claim 15 wherein in the double breast pump mode air is transmitted to a first breast via a first pathway defined by the first breast shield, the first conduit, the sixth port, the fifth port, a third conduit, the second port, the first port, and a fourth conduit between the first port and the pump and to a second breast via a second pathway defined by the second breast shield, the second conduit, the seventh port, the fifth port, the third conduit, the second port, the first port, and the fourth conduit.

* * * * *